United States Patent [19]

Rey et al.

[11] Patent Number: 4,721,095

[45] Date of Patent: Jan. 26, 1988

[54] DEVICE FOR CONTROLLING THE FLOW OF A FLUID AND A PROSTHETIC ORGAN EQUIPPED WITH THIS DEVICE

[75] Inventors: Pierre Rey, Thorigny; Jacqueline Leandri, Paris; Clement Abbou, Fontenay /s/ Bois, all of France

[73] Assignee: Centre National de la Recherche Scientifique, Paris, France

[21] Appl. No.: 650,496

[22] Filed: Sep. 14, 1984

[30] Foreign Application Priority Data

Sep. 14, 1983 [FR] France .................................. 83 14607

[51] Int. Cl.⁴ .......................... A61B 19/00; A61F 1/00
[52] U.S. Cl. ............................ 128/1 R; 128/DIG. 25; 128/346; 251/342; 623/12; 623/14
[58] Field of Search ................. 128/1 R, DIG. 25, 79, 128/346; 3/1, 1.2; 604/9, 247; 137/516.25–516.27, 219; 251/342; 623/12, 14

[56] References Cited

U.S. PATENT DOCUMENTS

| | | |
|---|---|---|
| 3,503,400 | 7/1967 | Osthagen . |
| 3,841,304 | 10/1974 | Jones . |
| 3,854,469 | 12/1974 | Giori et al. ................. 128/DIG. 25 |
| 4,407,278 | 10/1983 | Burton et al. ......................... 128/79 |
| 4,419,985 | 12/1983 | Trick .................................... 128/1 R |
| 4,457,299 | 7/1984 | Cornwell .................... 128/DIG. 25 |

FOREIGN PATENT DOCUMENTS

2373272 7/1978 France .

OTHER PUBLICATIONS

Kintzonidis, K., "Implantable Artificial Sphincter Ani", *Amer. Soc. Artif. Int. Organs,* vol. XVII, 1971.

*Primary Examiner*—Richard C. Pinkham
*Assistant Examiner*—Mary Ann Stoll Lastova
*Attorney, Agent, or Firm*—Oblon, Fisher, Spivak, McClelland, & Maier

[57] ABSTRACT

A device for controlling the flow of a fluid, more especially a biological fluid and in particular the urinary flow, the device including a rod which, in the rest condition, is sealingly clamped, by any appropriate clamping mechanism, inside a connecting tube, and which is made from a flexible plastic material presenting shrinkage on polymerization, and a mechanism which is adapted to prevent the axial movement of the valve rod along the connecting tube under the effect of the pressure of a fluid filling two flexible activating bags connected through the connecting tube, which may be incorporated with a third flexible bag. A prosthetic organ is formed by a urethral prosthesis of the interchangeable type including a tube made, for example, from silicon elastomer and a plurality of spurs formed on its outer surface and preventing any axial movement thereof, some of which are directed downwards, whereas the remainder are directed upwards, which prosthetic organ further includes, at the proximal end of the tube a mechanism providing sealing with respect to the bladder cooperates with the device for controlling the urinary.

10 Claims, 7 Drawing Figures

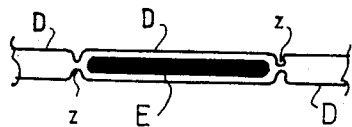
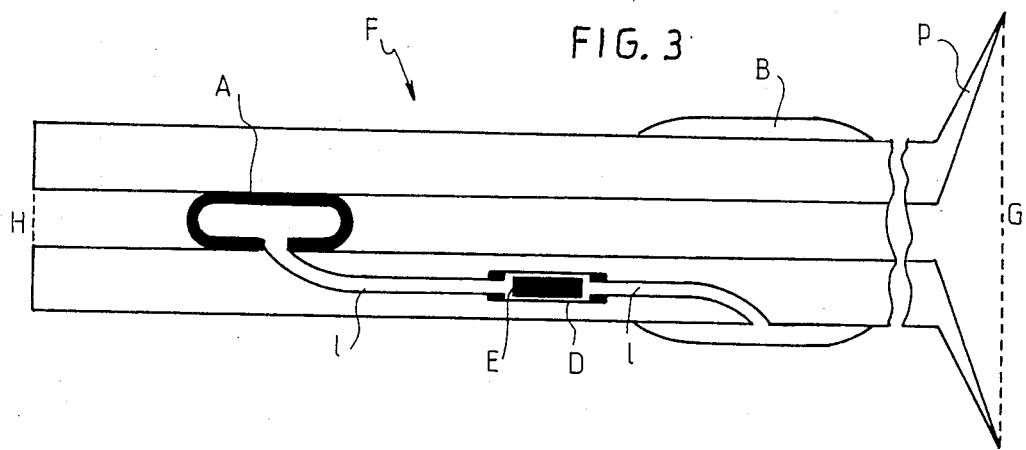
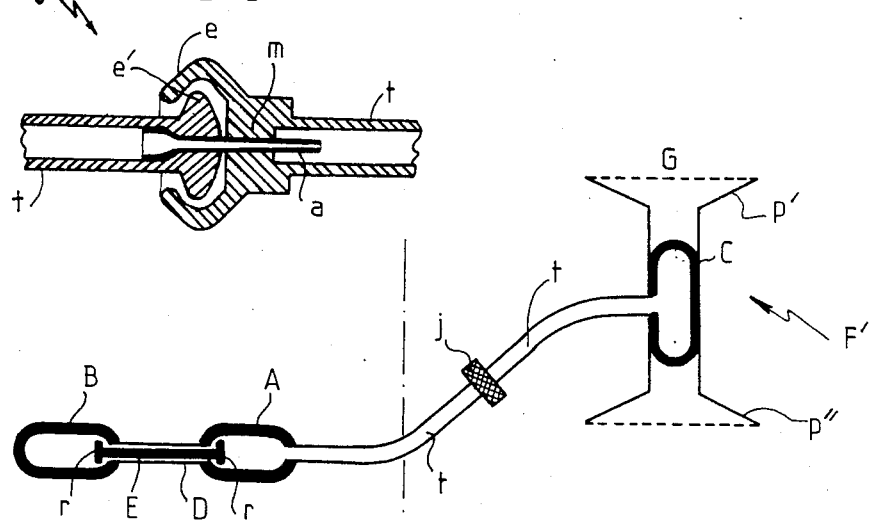

DEVICE FOR CONTROLLING THE FLOW OF A FLUID AND A PROSTHETIC ORGAN EQUIPPED WITH THIS DEVICE

BACKGROUND OF THE INVENTION

1. Field of the Invention

The present invention relates to a device for controlling the flow of a fluid, more especially a biological fluid and in particular the urinary flow, as well as a prosthetic organ equipped with this device and a process for manufacturing such a device.

2. Description of the Prior Art

French Pat. No. 2 251 302 describes a sphincteral prosthesis, implantable in an endo-urethral or ano-rectal position more especially, which is provided with an external activation mechanism of the electro-magnetic type, and more precisely, the regulation device intended to replace a damaged or deficient sphincter is formed by a tube portion housed in the natural duct concerned and by an inflatable bag inserted inside this tube portion, so that the aperture of this latter is closed off in the completely inflated condition, whereas the opening of this aperture is obtained by deflation of the bag.

Closing and opening of this tube portion, namely the inflation and deflation of said bag, are obtained by means of a fluid which fills the bag and an expansion chamber defined by a metal bellows and communicating with the bag through a flexible duct which is preferably surrounded by a bell mouthed sealing collar near the point of its implantation in the tube portion wherein the movements of this fluid are controlled by an electro-magnetic device acting through the skin. However, handling of this electro-magnetic control device is not very easy and its design is relatively heavy.

An artificial sphincter device with hydraulic control is also known which is described in French Pat. No. 2 373 272 and which comprises: a collar for clamping the urethra by inflation under the action of the pressurized liquid, at least one deformable reservoir for inflating said collar, a valve system disposed between this inflation reservoir and the clamping collar, and means for deflating said collar, possibly comprising an auxiliary deformable deflation reservoir.

This device comprises a single valve applied against a seat formed in a dividing wall provided inside a case and separating a first chamber—defined in cooperation with a first bottom of the case, more especially the one which is on the same side as the clamping collar—from a second chamber communicating with said deformable reservoir for inflating said collar, and means for controlling the deflation of said collar.

According to one embodiment of this sphincteral device which corresponds to the absence of said auxiliary deformable deflation reservoir, said dividing wall provided with the valve seat and the walls of said case are deflatable, so that they themselves form said means for controlling the deflation of the clamping collar, the single valve being in this case formed by a resilient, so deformable, tongue fixed to this dividing wall by one of its ends, and, the deformable case and said deformable inflation reservoir may be mounted on a rigid support. Said case comprises two pipes connected to said first and second bottoms, more precisely the first pipe connects said first chamber to said clamping collar whereas the second pipe connects the second chamber to said deformable inflation reservoir.

The main drawback of this second French patent resides in the fact that said resilient tongue is fixed to said dividing wall and in the fact that the separation from the normal application against its seat, during inflation of the collar by deformation of said reservoir, requires the application of a relatively high pressure, which justifies the use of said rigid support.

Furthermore, U.S. Pat. No. 3,854,469 describes a device for controlling the flow of a fluid through an anatomical duct through which flows a physiological fluid, such as urine through the urethra. This device comprises a first inflation means formed by a first flexible chamber containing, in the rest state, a sufficient amount of fluid to stop the flow of fluid in said anatomical duct when it is applied against the external wall of this duct, a valve means provided with a relatively narrow fluid passage which is sensitive to the hydrostatic pressure difference existing between the ends of this passage as well as to the pressure obtained by manual deformation of said first chamber, or of a second inflation means formed by a second flexible chamber which is connected to the first chamber by said valve means and which is intended to receive the fluid initially contained in this first chamber under the action of a pressure applied by manual deformation of this latter, the flow rate of the fluid from said first chamber to said second chamber being relatively high whereas the flow rate in the reverse direction (namely from said second chamber to the first one), under the action of the hydrostatic pressure difference existing between the first and second chambers, is relatively low and is cancelled out when the pressures between the two chambers are balanced out with, when the corresponding flow is cancelled, the closure of said fluid passage (the flow time under the action of said hydrostatic pressure difference depends on the dimensions—length and diameter—of this passage: this time may be reduced by exerting the pressure obtained by manual deformation also of the second chamber). Furthermore, this American patent states that the first chamber is maintained applied against the external wall of the duct, the flow rate of which it is desired to control, by means of a ribbon, the second chamber is provided with a natural rubber plug so that, if required, fluid may be added by hypodermic injection, and the valve means comprises a resilient body, made more especially from silicon elastomer which is dilatable under the action of the manipulations of said chambers for establishing a relatively high flow rate between these chambers.

The main disadvantage of this American patent is that it is also sensitive to the hydrostatic pressure difference existing between said two deformable chambers, which is not always desirable in this type of application. In addition, subcutaneous implantation thereof, like that of said second French patent, is relatively complicated.

A urethral prosthesis also exists which is placed in position through the endo-canalar path, and which is interchangeable (see the article in Annales d'Urologie, 1982, 16, No. 5 pages 285–288). This urethro prosthesis is formed by a tube about 15 cm in length and with a variable diameter, made from silicon elastomer.

This tube has anti adherent surfaces obtained by molding, two drain orifices situated at one centimeter from its proximal end, and a double plurality of studs preventing axial movement thereof, without however preventing manual extraction thereof, which are formed on the mean outer part of the tube and which are directed upwardly and downwardly respectively.

The uncontested advantage of this urethral prosthesis is that it may be changed, on request, without surgery; however, use thereof is limited to radic urethritis and to multiple recurring stenosis in man only and does not concern incontinence.

SUMMARY OF THE INVENTION

The present invention consequently provides a device for controlling the flow of the fluid, more especially a biological fluid and in particular the urinary flow, which may be implanted in a subcutaneous position, which answers better the requirements of practice than the devices of the prior art used for the same purpose, more especially in that handling thereof is very simple, in that possible implantation in a subcutaneous position is easy for the surgeon and represents a minimum of operating risks for the patient, as well as a minimum of alterations for this latter in so far as his anatomy and organic functions are concerned, and in that the effort required for using same is minimum. The present invention also provides interchangeable prosthetic organs, more especially urethral prostheses which answer better the requirements of practice than the prosthetic organs of the prior art used for the same purpose, and particularly in that they are equipped with a device for controlling the urinary flow in accordance with the arrangements of the present invention, so that, use thereof may extend to a large number of pathological cases relating to urinary incontinence, including incontinence of nervous origin and post operational incontinence (after surgical operations on the prostate in men more especially), they lend themselves, by said cooperation with the control device of the invention to forming urethral prostheses for use not only by men but also by women, and the prosthetic organ/flow control device assembly may be positioned without surgery in the case where the control device of the invention is incorporated in the walls of the prosthetic organ, in men more especially, or in the case where said control device extends from the urethro-vaginal canal, in women more especially.

The present invention provides then a device for controlling the flow of the fluid, more especially a biological fluid and in particular the urinary flow, of the type comprising:

either two flexible activating bags connected together by a connecting tube, made more especially from silicon elastomer, the first of which is intended to control, by deflation by manual deformation, the re-establishment of the flow of said biological fluid, whereas the second activating bag is intended to control, also by deflation by manual deformation, annulment of this flow;

or said two flexible activating bags connected together by said connecting tube and a third flexible bag, deflation and inflation of which, controlled by manual deformation of said first and second activating bags respectively, allow the flow of said biological fluid to be controlled, more especially by inserting this third bag in the aperture of the duct in which it is desired to control the flow, said third bag being connected more especially to the first activating bag by a first connecting tube of appropriate length, and a valve system of the type sensitive solely to the pressure obtained by manual deformation of one of said first and second activating bags, wherein said valve system comprises a rod which, in the rest state, is sealingly gripped, by any appropriate clamping means, inside said connecting tube, which is made from a flexible plastic material presenting shrinkage on polymerization, a means also being provided which is adapted to prevent axial movement of this valve rod along said connecting tube under the effect of said pressure.

According to an advantageous embodiment of the device of the invention, the means for clamping said rod is formed by a second tube disposed about said first tube.

According to another advantageous embodiment of the device of the invention, said clamping means is formed by at least one O seal.

According to another advantageous embodiment of the device of the invention, said clamping means is formed by a ring.

According to yet another advantageous embodiment, is formed by a spring.

According to a preferred embodiment of the device of the invention, said clamping means if formed by the wall itself of said tube.

According to an advantageous embodiment of the device of the invention, the means for preventing any axial movement of said rod is formed by a means selected from the group comprising:

a disk, or a cross piece, or a spur, or an element in the form of a "pig's tail", or else a sphere or ball, giving to said rod a dumb-bell configuration with which each end of said rod is provided, the means with which the two ends of said rod are provided being able to be identical or different. According to yet another advantageous embodiment of the device of the invention, the means preventing any axial movement of said rod is formed by a constriction of the diameter of said connecting tube at the level of the ends of said rod, obtained by molding.

In an advantageous variant of this embodiment, two auxiliary connecting tubes, with a diameter less than the diameter of said tube containing said rod and formed from the same material as said first and second flexible activating bags, connect said tube to said bags, thus preventing any axial movement of the rod which it contains.

In a further embodiment of the device of the invention, said first connecting pipe, connecting said third bag, comprises an intermediate cut-off and a rapid seal junction device, comprising more especially clips, reconstituting its physical continuity in the zone of said cut-off;

Besides the foregoing arrangements, the invention comprises other arrangements which will be clear from the following description.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1b refers to a variant of the device shown in FIG. 1a;

FIG. 1c shows the detail only of another variant; of the device of FIG. 1a;

FIG. 3 is the schematical representation of the application of the embodiment of the device shown in FIG. 1b, to an interchangeable uretheral prosthesis for masculine use, and FIG. 4 is the schematical representation of the application of the embodiment of the device shown in FIG. 2, to an interchangeable urethral prosthesis for feminine use.

DESCRIPTION OF THE PREFERRED EMBODIMENTS

Figure 1A:
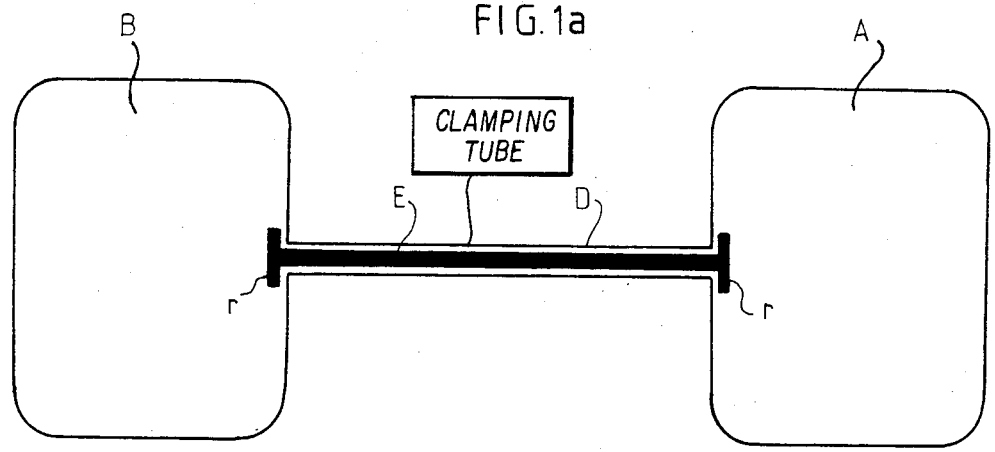
FIGS. 1a and 2 show schematicaly two different embodiments of the device for controlling the flow of a fluid, in accordance with the present invention.

FIG. 1a refers to a preferred embodiment of the device for controlling a flow of fluid, more especially a biological fluid and in particular the urinary flow, in accordance with the present invention.

This preferred embodiment is formed by a closed system filled with a fluid and comprising two flexible activating bags A and B connected together by a tube D whose wall is applied directly and sealingly to a rod E inserted inside said tube. However, other embodiments may be considered in which clamping of said rod E is provided by any means also ensuring sealing separation between the flexible activating bags, in the rest condition.

The axial movement of rod E in tube D is prevented by fitting, at each of the ends of said rod E, a disk r for example, as shown in FIG. 1a. For this, it is possible to give the ends of said rod E a different configuration, more especially that of a cross, a spur, a "pig's tail" or a sphere (or ball).

Figure 1B:
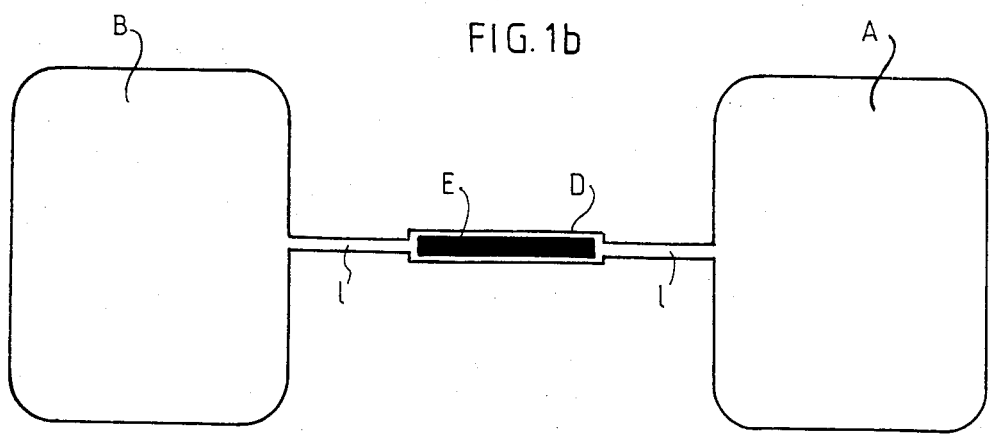

The same result may be further obtained: by connecting tube D to each of the two activating bags A and B by means of a pipe l whose diameter is less than the diameter of tube D, this variant being shown in FIG. 1b, or else, by forming a constriction by molding (cf. FIG. 1c) on said connecting tube D, at the level of the ends of rod E.

Since the two activating bags and tube D are formed from any flexible plastic material which shrinks on polymerization during curing, made from silicon or polyurethane preferably, more especially, tube D sealingly clamps round rod E which it contains, thus ensuring the sealed separation of the two bags A and B, whose volume is maximum in the rest position.

The operating principle of the flow control device rests on said sealing between two activating bags A and B, as well as on the resilience of the wall of tube D and on the tendancy of bags A and B to resume their original form when they are not being acted on. More precisely, an increased pressure for example in bag A, obtained by manual or finger pressure, causes the wall of tube D to move away from the surface of rod E and, consequently, causes the compressed fluid contained in bag A to pass to bag B, where the fluid is stored.

When the pressure exerted on bag A is released, the fluid stored at B does not come back spontaneously to A because, although this latter tends to resume its initial shape, tube D opposes this movement however by sealingly tightening around rod E, which causes depression of bag A and so suction of fluid from bag A towards bag B, namely deflation of the first bag A. It is evident that an increase in pressure in bag B causes the reverse phenomenon and the transfer of fluid from B to A, and so deflation of bag B and inflation of bag A.

It will be readily understood from the foregoing that if, for example, activating bag A is inserted in a duct, it is possible to open and close, respectively, the aperture of this duct by proceeding in the above described way, namely by alternately compressing the two activating bags A and B: it goes without saying that the shape of one of the two bags (in this case that of bag B) may have any form, for example spherical, annular or other, but in any case such that it may be adapted to the different applications to which the control device of the invention is likely to be put, whereas the shape of the other bag (in this case bag A) must be able to be adapted, in the rest condition, to the shape of the duct which it is to close, so as to be able to fulfill both the role of activating bag and closure bag of the conduct whose flow is to be controlled.

A very interesting application of this control possibility is shown in FIG. 3, in which F represents an interchangeable urethral prosthesis for masculine use, of the type comprising a silicon elastomer tube, preferably, provided with spurs (not shown) which prevent axial movement thereof. This prosthesis is equipped with a device for controlling the urinary flow in accordance with the first embodiment of the device of the invention, shown in FIG. 1b.

The tube D for clamping rod E is inserted in the wall of the interchangeable urethral prosthesis F a bag A is inserted inside the duct of the prosthesis F, upstream of the urinary meatus H, whereas an annular bag B is placed externally of the duct of this prosthesis F, about the vesical end which is advantageously provided with a bell-mouth collar P, at the proximal end, ensuring sealing with respect to the bladder G, each of the two bags A and B being connected to tube T by a pipe l also inserted in the wall of the prosthesis F.

The operation of the interchangeable prosthetic urethra F, placed in the penis, is as follows. Pressure on the penis in the zone of bag A causes the transfer of the fluid which is contained therein towards bag B. Release of the pressure on bag A causes the aperture of the prosthetic urethra F to open; this opening persists, which allows urination. Then, as soon as urination is finished, pressure on the penis in the zone of bag B causes the fluid which is contained therein to flow back towards bag A. Release of the pressure on bag B causes the aperture of the urethral prosthesis F to close by complete inflation of bag A.

Figure 2:
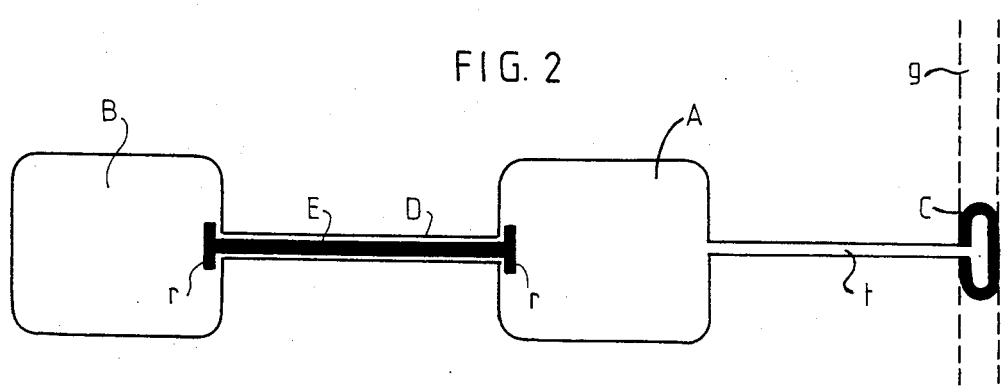

FIG. 2 refers to a second embodiment of the device of the invention for controlling the flow of a fluid. This second embodiment is formed by a closed system filled with a fluid and comprising, like the control device of the first embodiment shown in FIG. 1a, two activating bags A and B connected together directly by a tube D which clamps round a rod E in the form of a dumb bell. This second embodiment further comprises a third bag C connected to bag A by connecting pipe t and intended to close the aperture of a duct g, of an artificial sphincter more especially.

The operating principle in this second case is the same as that of the device shown in FIG. 1a and of the variant thereof shown in FIG. 1b insofar as a pressure on the first activating bag A causes an increase of the pressure inside this latter, as well as inside the closure bag C—because of the communication therebetween through a third connecting pipe t—and, consequently, the wall of tube D moves away from the surface of rod E and the compressed fluid contained in bags A and C passes towards bag B where the fluid is stored.

When the pressure exerted on bag A is released, the depression which is created in the latter (as explained above) causes suction of the fluid contained in bag C towards the first activating bag A and so deflation of the closure bag C and opening of duct g. Conversely, simple pressure on the second activating bag B results in increasing the pressure in this latter, causing the transfer of the fluid from B to A and C, and so inflation of the closure bag C and closure of duct g.

Insofar as the connecting pipe t between bags A and C is concerned, it may advantageously comprise an intermediate cut-off and a sealed rapid junction device j (cf. FIG. 4) reconstituting its physical continuity in the zone of this cut-off.

This sealed rapid junction device j is advantageously of the clip type, as shown in FIG. 5. The end of the section of pipe t which is on the same side as the activating bags A and B is provided with a bulge portion e' cooperating with a needle (a) which passes therethrough and which is secured to this bulge portion and to the end part of said tube section t. Insofar as the end of the upper section of pipe t is concerned, such is provided with a cap e, snap fitted onto bulge portion e', and a central sleeve m which is axially pierced so as to receive said needle A during snap fitting, thus sealingly reconstituting the physical continuity required between the two sections of said pipe t.

Another very interesting application of the possibility of controlling the opening of a duct, provided with the device of the invention and similar to the one shown in FIG. 3 is shown in FIG. 4 wherein F' represents an interchangeable urethral prosthesis for feminine use, which is also of the type comprising a silicon elastomer tube, preferably provided with spurs (not shown), on its outer surface for preventing axial movement thereof.

This prosthesis F' has, like the prosthesis for masculine use F, a collar p' at its proximal end, for providing sealing with respect to the bladder G. In this respect, it should be emphasised that sealing may be also obtained (in both cases of use of the urethral prosthesis), in an advantageous variant, by means of an annular bag (not shown) surrounding the proximal end of the prosthetic tube which is introduced into the bladder G in the manner of a Foley probe.

The prosthesis F' also has another collar p" at its distal end, considering the anatomical differences related to the feminine use of the urethral prosthesis F', which cooperates also in this case with a urinary flow control device, in accordance with the second embodiment of the device of the invention shown in FIG. 2, which control device is implantable in a subcutaneous position, so that the urethral prosthesis/control device assembly forms a partially interchangeable model, insofar as the prosthetic urethra F' is concerned.

It is again found in FIG. 4, in zone I corresponding to subcutaneous implantation, the control device of FIG. 2 whereas the zone II, which is separated from zone I by a discontinuous line, corresponds to the urethral prosthesis F' in the urethro-vaginal position: a sealed rapid junction device j, more especially a clip device, of the type already described, is provided in the urethro-vaginal portion of the connecting pipe t, between activating bag A and closure bag C, so as to facilitate the interchangeability of the urethro prosthesis F' without touching the implanted activating device. The implantation zone I is chosen, as is evident, so that the person concerned cannot accidentally exert a pressure thereon.

Alternately, a completely interchangeable urethral prosthesis/control device assembly may be used, as in the case of masculine use (cf. FIG. 3), provided that the prosthetic assembly containing the opening and closure mechanism is in a vaginal position possibly extending from the vagina. On the other hand, in some cases, it may be necessary to provide subcutaneous implantation of the urinary flow control device cooperating with a urethral prosthesis F for masculine use, according to the principle illustrated during the description of the urethral prosthesis F' for feminine use. It goes without saying that the control device is also applicable to the implantable sphincteral prosthesis described in Pat. No. 2,251,302, as well as to any other appropriate prosthetic organ.

For obtaining sealing clamping, in the rest condition, between tube D and rod E which it contains this is provided, for each embodiment (cf. FIGS. 1a, 1b and 2), as well as the applications of these embodiments (shown in FIGS. 3 and 4), through the process of molding a silicon elastomer preferably, or polyurethane more especially, or in general, any other flexible plastic material presenting a shrinkage on polymerization during curing, this plastic material is molded about rod E which is previously positioned in a mold and which is surrounded, after molding, by the clamping tube D thus molded.

Insofar as the manufacture of the overall control device of the invention is concerned, it may take place, for example, according to one of the two following methods. In a first method, the flexible activating bags A and B are formed and the flexible closure bag C if required, as well as the connecting tubes l and t, separately from the clamping tube D, the assembly of these elements together and with this tube D, so as to obtain a closed assembly to be filled with a fluid, being then obtained by molding, by bonding or vulcanization or similar. In a second method, the different elements forming said closed assembly are integrally molded with tube D, which involves the use of the same material for forming these component elements.

As is clear from the foregoing, the invention is in no manner limited to those of its embodiments, modes of implementation and application which have just been described more explicitly and embraces on the contrary all variants thereof which may occur to a technician skilled in the matter, without for all that departing from the scope and spirit of the present invention.

What is claimed is:

1. A device for controlling the flow of a fluid in a duct, comprising:
   first and second flexible activating bags containing an activating fluid;
   a connecting tube for connecting said first and second bags;
   valve means responsive solely to the pressure of said activating fluid obtained by manual deformation of one of said first and second activation bags,
   said valve means comprising a valve seat in the form of a rod located inside said connecting tube,
   wherein said connecting tube comprises a valve element formed of a flexible plastic material for sealing clamping said rod,
   said first bag being adapted to effect upon deflation by manual deformation, the re-establishment of the flow of fluid in a duct, whereas the second activating bag is adapted to effect, also by deflation by manual deformation, cancelling of said flow;
   clamp means for reinforcing the sealing clamping of said rod in a rest condition inside said connecting tube, and
   means for preventing said rod from leaving said connecting tube under the effect of said pressure wherein the clamping action of said connecting tube and said clamp means is overcome solely by said pressure.

2. A device for controlling the flow of a fluid in a duct, comprising:

first and second flexible bags containing an activating fluid;

a first connecting tube for interconnecting said first and second bags containing an activating fluid;

a third flexible bag communicating with said first and second activating bags;

a connecting pipe for connecting said third bag to one of said first and second activating bags;

valve means responsive solely to the pressure of said activating fluid obtained by manual deformation of one of said first and second activating bags, said valve means comprising a valve seat in the form of a rod located inside said connecting tube, wherein said connecting tube comprises a valve element for sealingly clamping said rod formed of a flexible plastic material, said first bag being adapted to effect, upon deflation by manual deformation, the re-establishment of the flow of fluid in a duct, whereas the second activating bag is adapted to effect, also by deflation by manual deformation, cancelling of said flow, wherein said third flexible bag is adapted to be inserted inside said duct in order to control the flow of said fluid through its deflation and inflation;

clamp means for reinforcing the sealing clamping of said rod in a rest condition inside said connecting tube, and means for preventing said rod from leaving the connecting tube under the effect of said pressure, wherein the clamping action of said connecting tube and said clamp means is overcome solely by said pressure.

3. The device as claimed in anyone of claims 1 or 2, therein the means for clamping said rod further comprises a second tube disposed about said connecting tube.

4. The device as claimed in anyone of claims 1 or 2, wherein said clamping means further comprises at least one O seal disposed about said connecting tube.

5. The device as claimed in anyone of claims 1 or 2, wherein said clamping means further comprises at least one ring disposed about said connecting tube.

6. The device as claimed in anyone of claims 1 or 2, wherein said clamping means further comprises at least one spring disposed about said connecting tube.

7. The device as claimed in anyone of claims 1 or 2, wherein said clamping means further comprises a wall of said connecting tube.

8. The device as claimed in anyone of claims 1 or 2, wherein the means for preventing said rod from leaving said connecting tube under the effect of said pressure further comprises a cross piece.

9. The device as claimed in anyone of claims 1 or 2, wherein the means for preventing said rod from leaving said connecting tube under the effect of said pressure further comprises a spur.

10. The device as claimed in claim 2, wherein said connecting pipe connecting said third bag to one of said first and second activating bags further comprises an intermediate cut off and sealed quick junction device.

* * * * *